United States Patent
Taylor

(10) Patent No.: US 10,478,182 B2
(45) Date of Patent: Nov. 19, 2019

(54) SURGICAL DEVICE IDENTIFICATION

(71) Applicant: Covidien LP, Mansfield, MA (US)

(72) Inventor: Joseph Taylor, Newtown, CT (US)

(73) Assignee: Covidien LP, Mansfield, MA (US)

(*) Notice: Subject to any disclaimer, the term of this patent is extended or adjusted under 35 U.S.C. 154(b) by 304 days.

(21) Appl. No.: 13/961,983

(22) Filed: Aug. 8, 2013

(65) Prior Publication Data

US 2014/0110456 A1 Apr. 24, 2014

Related U.S. Application Data

(60) Provisional application No. 61/715,480, filed on Oct. 18, 2012.

(51) Int. Cl.
| | | |
|---|---|---|
| *A61B 17/072* | (2006.01) | |
| *A61B 90/90* | (2016.01) | |
| *A61B 17/00* | (2006.01) | |
| *A61B 90/00* | (2016.01) | |

(52) U.S. Cl.
CPC ............ *A61B 17/072* (2013.01); *A61B 90/90* (2016.02); *A61B 90/03* (2016.02); *A61B 2017/00119* (2013.01); *A61B 2017/00398* (2013.01); *A61B 2017/00464* (2013.01); *A61B 2017/07221* (2013.01); *A61B 2017/07257* (2013.01); *A61B 2017/07271* (2013.01); *A61B 2090/0807* (2016.02); *A61B 2090/0811* (2016.02)

(58) Field of Classification Search
CPC ........ A61B 17/072; A61B 2017/00119; A61B 2017/00473
USPC ............................................ 227/175.1, 176.1
See application file for complete search history.

(56) References Cited

U.S. PATENT DOCUMENTS

| | | | |
|---|---|---|---|
| 5,395,033 A | 3/1995 | Byrne et al. | |
| 5,464,144 A * | 11/1995 | Guy ..................... | A61B 17/072 128/104.1 |
| 5,693,042 A | 12/1997 | Boiarski et al. | |
| 6,846,307 B2 | 1/2005 | Whitman et al. | |
| 6,953,139 B2 * | 10/2005 | Milliman ......... | A61B 17/07207 227/175.1 |

(Continued)

FOREIGN PATENT DOCUMENTS

| | | |
|---|---|---|
| CN | 102217961 A | 10/2011 |
| EP | 1 728 475 | 12/2006 |

(Continued)

OTHER PUBLICATIONS

Extended European Search Report corresponding to EP 13 18 9258.0, completed Jan. 30, 2014 and dated Feb. 7, 2014; (8 pp).

(Continued)

*Primary Examiner* — Chelsea E Stinson

(57) ABSTRACT

A surgical device is disclosed, which has a loading unit having a cartridge assembly, anvil assembly, and a stapling drive member with a flange that engages at least one of the cartridge assembly and anvil assembly, the loading unit having a body portion; and a mechanical feature on the at least one of the cartridge assembly and anvil assembly, the mechanical feature being arranged to be engaged by the flange, the mechanical feature being indicative of an aspect of the loading unit. The mechanical feature can indicate the staple line length, staple size, type of loading unit, and/or whether the loading unit has been fired, for a surgical stapling device.

23 Claims, 10 Drawing Sheets

(56) References Cited

U.S. PATENT DOCUMENTS

| | | | |
|---|---|---|---|
| 7,044,353 B2 | 5/2006 | Mastri et al. | |
| 7,565,993 B2 | 7/2009 | Milliman et al. | |
| 7,887,530 B2 | 2/2011 | Zemlok et al. | |
| 8,517,241 B2 * | 8/2013 | Nicholas | A61B 17/07207 227/175.1 |
| 8,960,520 B2 * | 2/2015 | McCuen | A61B 17/07207 227/175.1 |
| 2004/0232201 A1 * | 11/2004 | Wenchell | A61B 17/07207 227/176.1 |
| 2006/0273135 A1 * | 12/2006 | Beetel | A61B 17/068 227/175.1 |
| 2008/0078808 A1 * | 4/2008 | Hess | A61B 17/0644 227/181.1 |
| 2008/0083812 A1 | 4/2008 | Scirica | |
| 2009/0090763 A1 | 4/2009 | Zemlok et al. | |
| 2009/0108048 A1 * | 4/2009 | Zemlok | A61B 17/07207 227/175.1 |
| 2010/0094091 A1 * | 4/2010 | Cappola | A61B 17/072 600/137 |
| 2011/0017801 A1 * | 1/2011 | Zemlok | A61B 17/07207 227/175.1 |
| 2011/0036887 A1 * | 2/2011 | Zemlok | A61B 17/07207 227/175.1 |
| 2011/0139851 A1 * | 6/2011 | McCuen | A61B 17/07207 227/175.1 |
| 2011/0174099 A1 * | 7/2011 | Ross | A61B 17/072 74/89.32 |
| 2011/0290855 A1 * | 12/2011 | Moore | A61B 17/072 227/180.1 |
| 2012/0211542 A1 * | 8/2012 | Racenet | A61B 17/07207 227/175.1 |
| 2012/0228358 A1 * | 9/2012 | Zemlok | A61B 17/072 227/176.1 |

FOREIGN PATENT DOCUMENTS

| | | |
|---|---|---|
| EP | 1728475 A2 | 12/2006 |
| EP | 1908414 | 9/2008 |
| EP | 2 364 651 | 9/2011 |
| EP | 2 377 472 | 10/2011 |
| EP | 2377472 A1 | 10/2011 |
| JP | 7-51273 | 2/1995 |
| JP | 2009090113 A | 4/2009 |
| JP | 2011-36656 A | 2/2011 |

OTHER PUBLICATIONS

Chinese First Office Action corresponding to counterpart Int'l Appn. No. CN 2013104928626 dated Sep. 26, 2016.
Extended European Search Report corresponding to counterpart Int'l Appln. No. EP 16 17 8794.0 dated Oct. 11, 2016.
Chinese Second Office Action corresponding to counterpart Int'l Appln. No. CN 2013104928626 dated Apr. 25, 2017.
Australian Examination Report No. 1 corresponding to counterpart Int'l Appln. No. AU 2013221931 dated May 11, 2017.
Japanese Office Action corresponding to counterpart Int'l Appln. No. JP 2013-188081 dated Jun. 22, 2017.
Australian Examination Report No. 2 corresponding to counterpart Australian Patent Appln. No. AU 2013221931 dated Feb. 2, 2018.
Japanese Office Action corresponding to counterpart Patent Appln. JP 2013-188081 dated Apr. 9, 2018.
European Office Action corresponding to counterpart Patent Appln. EP 16 17 8794.0 dated Apr. 19, 2018.
Canadian Office Action dated May 3, 2019 corresponding to counterpart Patent Application CA 2825706.

* cited by examiner

SURGICAL DEVICE IDENTIFICATION

CROSS-REFERENCE TO RELATED APPLICATIONS

This application claims the benefit and priority to U.S. Provisional Patent Application Ser. No. 61/715,480, filed Oct. 18, 2012, the entire disclosure of which is incorporated by reference herein.

TECHNICAL FIELD

The present disclosure is directed to surgical devices, such as surgical stapling instruments, that have a handle portion and a removable and replaceable end effector. In particular, the present disclosure relates to surgical devices and end effectors having sensors for identifying the type of end effector.

BACKGROUND

Surgical devices having a handle portion and a replaceable unit are known. A surgical device that can be used to fire different types and sizes of loading units is disclosed in U.S. Pat. No. 7,044,353 to Mastri et al. ("Mastri"), the disclosure of which is hereby incorporated by reference in its entirety. In Mastri, the loading units can have different sized surgical staples and, further, different staple line lengths. U.S. Pat. No. 7,565,993 to Milliman et al. discloses articulating and non-articulating loading units that can be used with a handle portion, the disclosure of which is hereby incorporated by reference in its entirety.

Surgical devices having an adapter assembly and a plurality of surgical end effectors that can be attached thereto are disclosed in U.S. Publication No. 2011-0174099, which is hereby incorporated by reference in its entirety. The adapter is used to enable a powered motorized hand held driver to connect to a variety of end effectors, such as an end to end anastomosis end effector, or circular stapler, an endoscopic gastrointestinal anastomosis end effector, such as a linear endoscopic stapler, or a transverse anastomosis end effector. Powered surgical devices having a remote power console have also been proposed, as disclosed by U.S. Pat. No. 6,846,307 to Whitman et al. ("Whitman"), which is hereby incorporated by reference in its entirety. Whitman discloses a controller in the console for controlling the surgical device. The controller can have a memory unit, including RAM and ROM, and reads data from the particular end effector attached to the controller. The controller can read identification data from a memory unit on the end effector attached to the controller and then, by virtue of the controller's connection to the motors of the surgical device, control the operation of the surgical device.

A powered surgical instrument is disclosed by U.S. Pat. No. 7,887,530 to Zemlok et al., the entire disclosure of which is hereby incorporated by reference herein, utilizes a shift motor to drive multiple functions of the instrument. A variety of sensors is disclosed.

In the context of surgical devices designed to be used with a variety of removable and replaceable end effectors or loading units, it is desirable to identify the type of end effector or loading unit that is attached. This information can be used to determine how to operate the surgical device.

SUMMARY

In an aspect of the present disclosure, a surgical device comprises a loading unit having a cartridge assembly, anvil assembly, and a stapling drive member. The stapling drive member has a flange that engages at least one of the cartridge assembly and anvil assembly, and the loading unit includes a body portion. There is a mechanical feature on the at least one of the cartridge assembly and anvil assembly, the mechanical feature being arranged to be engaged by the flange. The mechanical feature is indicative of an aspect of the loading unit.

The surgical device can further comprise a handle portion and an elongate portion. The elongate portion can be an adapter assembly having a distal end for removably connecting to the loading unit and a proximal end for removably connecting to the handle portion. The elongate portion can have at least one drive member for connecting to and driving the stapling drive member. The handle portion can have a controller.

In certain embodiments, the loading unit has a sensor for determining the gap between the anvil assembly and cartridge assembly.

The handle portion can include a motor with an output shaft. The handle portion can include a sensor for determining the torque on the output shaft of the motor. The controller can include a memory unit.

The loading unit may have a sensor for determining clamping pressure. In certain embodiments, the clamping pressure is saved in the memory unit of the controller.

The mechanical feature may be a coating, a texture, a depression, or a protrusion. The mechanical feature can be depressions, depressions and protrusions, or protrusions.

In certain embodiments, the anvil assembly includes an anvil with a ramped surface. The mechanical feature may be defined on the ramped surface.

The mechanical feature may be proximal to the ramped surface.

In certain embodiments, the cartridge assembly has a channel. The mechanical feature may be defined on the channel.

The controller may save data concerning the use of the surgical device.

The cartridge assembly may have linear rows of staples. In certain embodiments, the mechanical feature indicates a length of the linear rows. The mechanical feature can indicate the size of the staples.

BRIEF DESCRIPTION OF THE DRAWINGS

Embodiments of the presently disclosed surgical device are disclosed herein, with reference to the following drawings.

DETAILED DESCRIPTION

Figure 1:
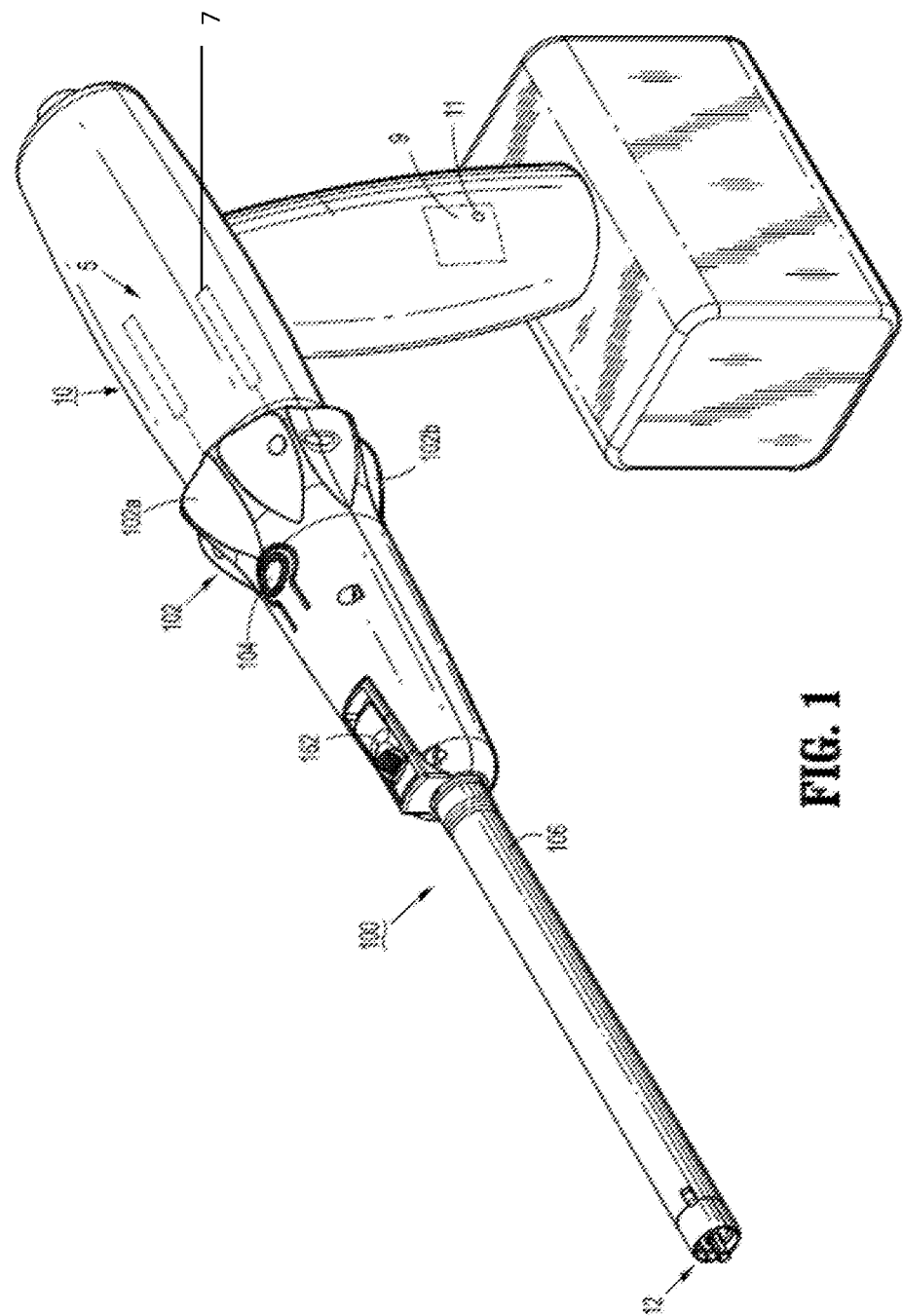
FIG. 1 is a perspective view of the handle portion according to certain embodiments of the disclosure.
Figure 1A:
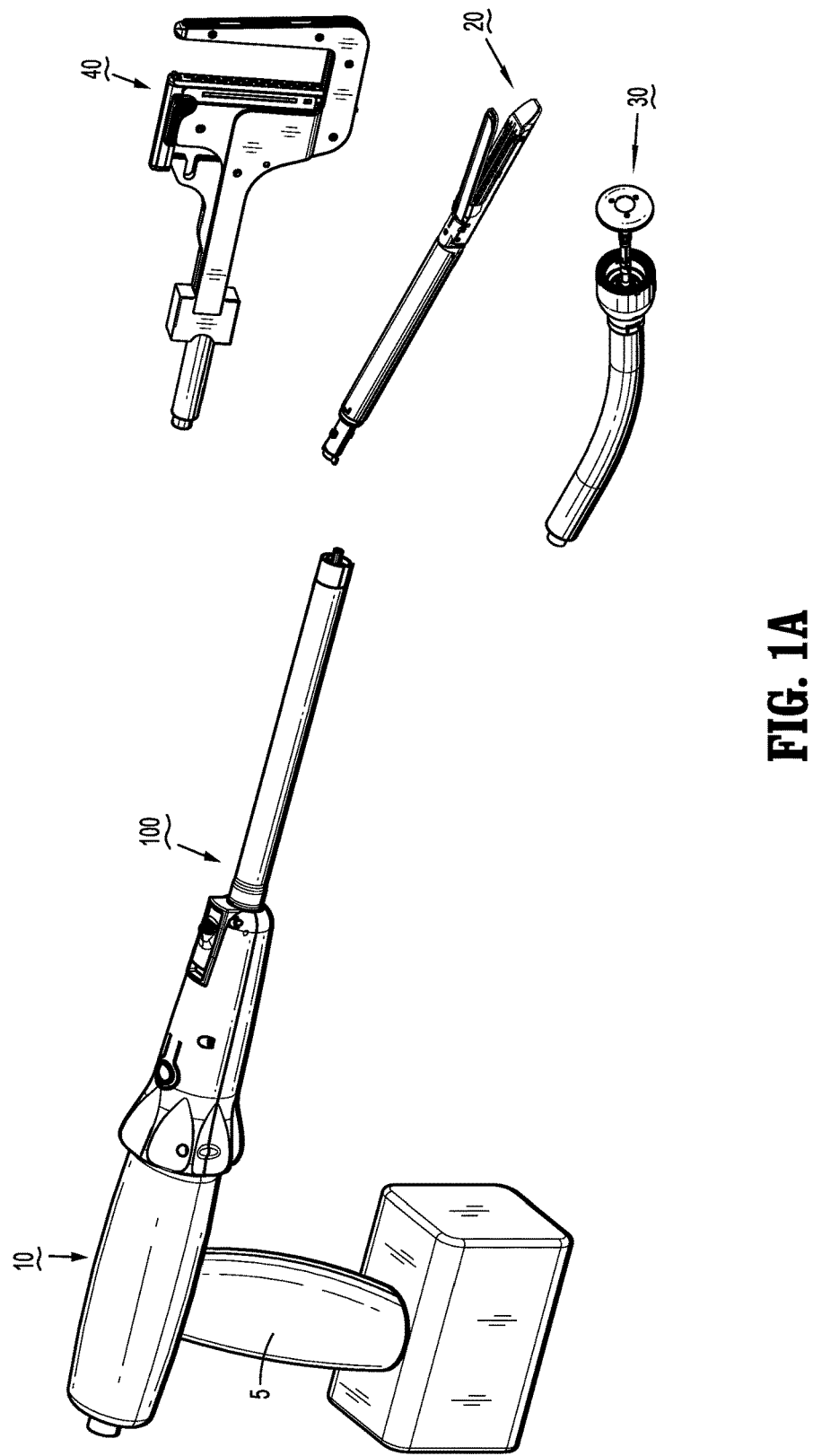
FIG. 1A is a perspective view of a handle portion and loading units according to certain embodiments of the disclosure.
Figure 2:
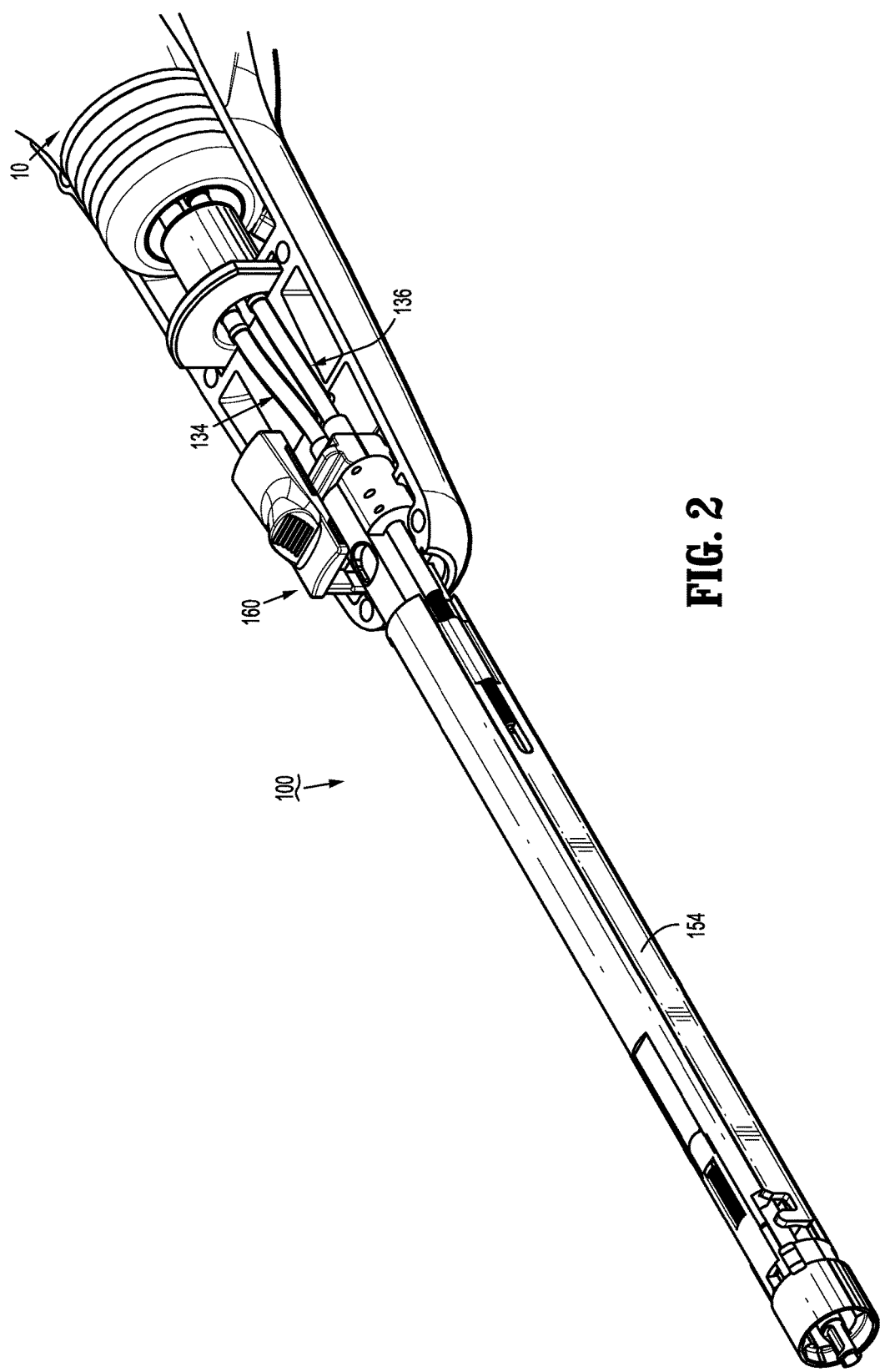
FIG. 2 is a perspective view of an adapter attached to a handle portion, with some parts removed according to certain embodiments of the disclosure.

Persons having skill in the art will understand the present invention from reading the following description in conjunction with the accompanying drawings. Reference characters indicate the same or similar elements throughout the drawings. As is customary, the term "distal" refers to a location farther from the user of the instrument and the term "proximal" refers to a location that is closer to the user of the instrument.

A surgical device having a handle portion 10, and a plurality of removable and replaceable loading units, is shown in FIGS. 1 through 6. The surgical device includes an elongate portion. For example, the handle portion 10 may have an endoscopic shaft that forms part of the handle portion 10 or the handle portion 10 may be connected to an adapter assembly 100 that includes an outer tube 106 and release button 104 having a latch for removably connecting the adapter assembly to the handle portion 10. Alternatively, the connection can be a threaded connection, bayonet connection or any other connection. The distal end of the endoscopic shaft, or the distal end of the adapter assembly 100, has a connection portion 12 for forming a connection to a loading unit. Loading units 20, 30 and 40 are shown. Although a linear endoscopic stapling loading unit 20 is described in detail, a circular stapling 30 or a transverse stapling 40 loading unit may also be attached to the surgical device. Loading units incorporating electrical energy, ultrasonic energy, or other energy can also be provided. Appropriate adapter assemblies are provided to accommodate the various loading units. For example, it may be desirable to provide three drive shafts for operating the circular stapling loading unit 30. An adapter assembly having three drive shafts therein could be used to separately drive the opening and closing of the anvil to grasp tissue, the driving of the staples through tissue and against the anvil, and the cutting of tissue.

Figure 3:
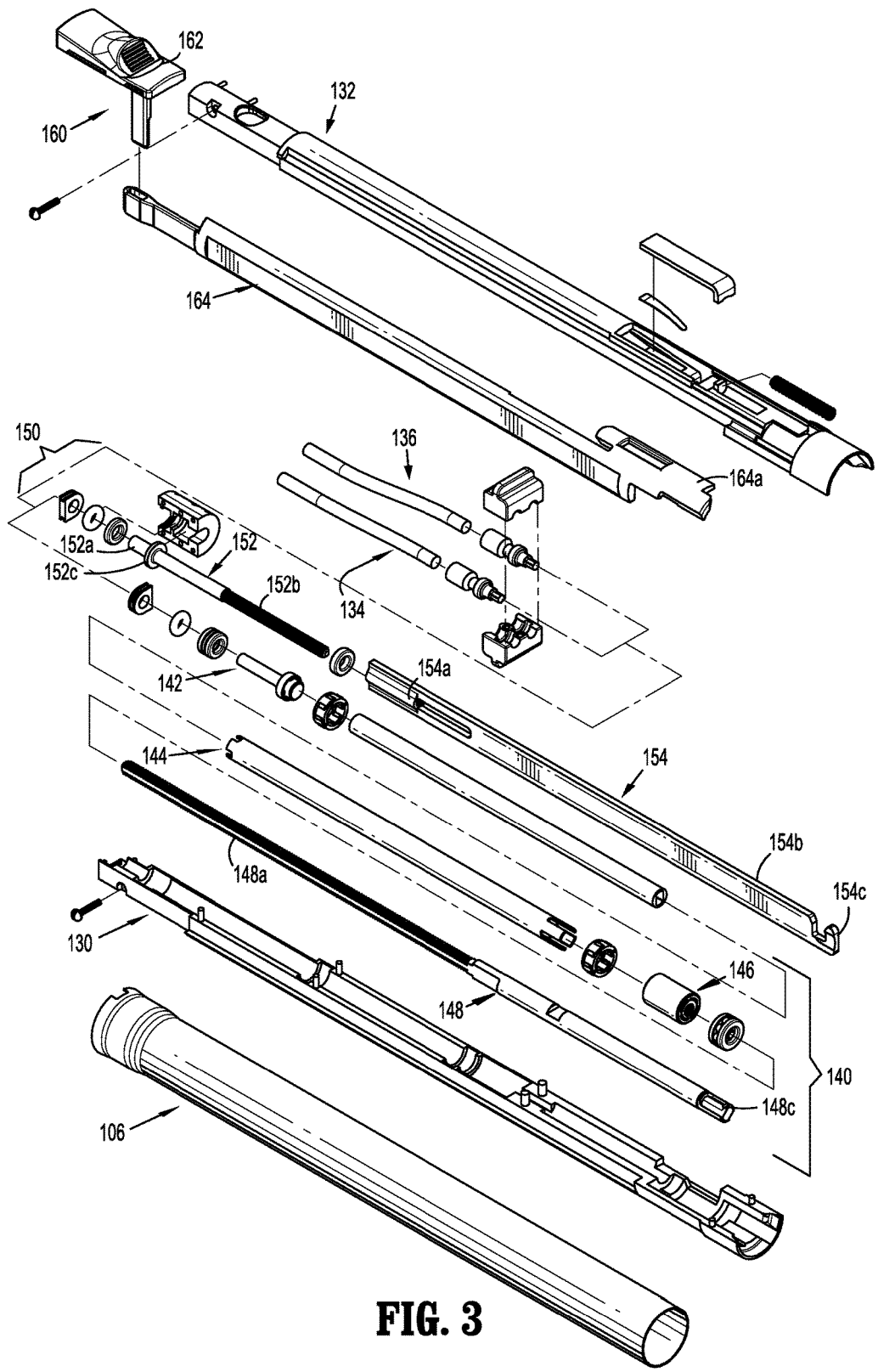
FIG. 3 is an exploded perspective view of an adapter according to certain embodiments of the disclosure.
Figure 4:
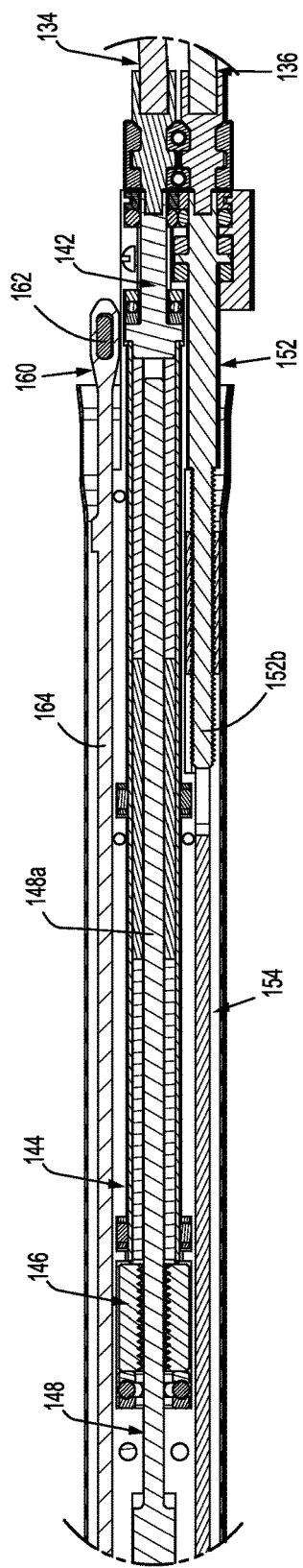
FIG. 4 is a cross sectional view of part of an adapter according to certain embodiments of the disclosure.

The adapter assembly 100 that is used with the loading unit 20 has a body 130 and two drivers: an articulation drive cable 136 and a stapling drive cable 134. As best seen in FIG. 3, the adapter assembly 100 has a drive converter assembly for each of the drive shafts, to convert rotational motion of the output from the motor assembly 5 to linear translation of the drive members of the adapter assembly. For example, the first drive converter assembly 150 has a first shaft 152 that connects to a first output from the motor assembly 5 via the drive cable 136. The first shaft 152 includes a threaded distal end 152b. The articulation drive bar 154 has an internally threaded collar 154a that is engaged with the threaded distal end of the first shaft 152. The threaded distal end 154a is long enough to translate the articulation drive bar 154 a desired distance.

The second drive converter assembly 140 has a second shaft 148 that connects to a second output from the motor assembly 5, through the stapling drive cable 134. The second shaft 148 includes a threaded proximal end 148a. An internally threaded collar 146 is engaged with the threaded proximal end 148a of the second shaft. The collar 146 is connected to a tubular sleeve 144. A proximal coupling 142 connects the drive cable 134 to the tubular sleeve 144. As the drive cable 134 rotates, the tubular sleeve 144 and collar 146 are rotated and the second shaft 148 is advanced in a distal direction. The threaded proximal end 148a is long enough to translate the second or stapling drive shaft 148 a desired distance for clamping of tissue and firing staples. In any of the embodiments disclosed herein, the drive converter assembly can have shafts that are internally threaded and the articulation drive shaft and/or stapling drive shaft can have an end that forms a threaded rod to engage and interact with the internally threaded member.

The motor assembly 5 can be separate from the surgical device, but is desirably part of the handle portion 10. One or more motors are used. For example, two dual directional motors can be mounted in the handle portion 10 and connected to a power source which may be a battery internal or external to the handle portion 10. Each motor can be connected to a switch on the handle portion and an additional switch for reversing the direction of the motors can be provided on the handle portion as well. The power source is desirably a removable and rechargeable direct current battery, but alternative sources, such as a remote access outlet for alternating current supply, can be used. A transformer or gear set can be used to adapt the power source for the motors.

The distal end of the adapter assembly 100 has a connection portion 12 for removably connecting to the loading unit 20. The connection portion 12 may essentially form a bayonet connection, like that described in U.S. Pat. No. 7,044,353 to Mastri et al., the disclosure of which is hereby incorporated by reference herein in its entirety. A locking member 164 for securing the loading unit 20 unto the adapter assembly 100 is connected to a button 162. The button 162 is spring biased to a locked position to prevent removal of the loading unit until the button is moved to an unlocked position.

The endoscopic linear stapling loading unit can be like those described in Mastri or Millman et al., U.S. Pat. No. 7,565,993, the disclosures of which are hereby incorporated by reference herein. The loading unit 20 has an elongate body portion 200 with a proximal end 258 defining two lugs 254 for forming a connection with a shaft of an adapter assembly 100 or a handle portion. Other means of connecting the loading unit can be used. The loading units can be designed to be attached to either a powered, motorized surgical driver or manually actuated handle. An end 164a of the locking member 164 of the connection portion of the adapter assembly 100 (see FIG. 3) engages the lugs 254 of the loading unit to secure it in place. A tube 251 is disposed around the body 200.

The loading unit 20 has an articulation link 256 with a hooked proximal end 258 for engaging a hooked distal end 154c of the articulation drive bar 154. An axial drive assembly has a proximal pusher 201 for engaging the stapling drive shaft 148. Each of the stapling drive shaft 148 and articulation drive bar 154 are driven by their respective outputs from the motor assembly and, by virtue of the drive converter assemblies, are translated axially in a distal direction.

The axial drive assembly has a stapling drive member 211 that includes a drive beam 212 and clamping member 213 at a distal end of the drive beam 212. (See FIG. 6). The drive beam 212 may be an elongate sheet of material or a series of stacked sheets of material that form the clamping member at a distal end thereof. The clamping member 213 is a member that has an upper flange or roller member 214 and a lower flange 216 (see FIG. 5) attached to a vertical portion 215 that has a knife blade. The proximal portion of the drive beam 212 has an opening for carrying the pusher 201 so that the stapling drive shaft 148 will drive movement of the axial drive assembly distally. The clamping member 213 may have molded pieces of plastic, or another plastic coating, for reducing the friction that will occur during clamping and stapling. See EP 1,908,414 and U.S. Publication No. 2008/0083812, the disclosures of which are hereby incorporated by reference herein.

A pair of jaws are attached to the elongate body 200 via a mounting portion 236. A stapler anvil assembly 207 includes an anvil 204 and cover 208. The anvil 204 defines a slot 214 and a ramped surface 209. The cartridge assembly 230 includes a staple cartridge 220, channel 218 and a firing assembly for interacting with the drive beam 212 and clamping member 213. The channel 218 also defines a slot (not shown) that allows the vertical portion 215 extend through the slot and locate the lower flange 216 below the channel 218. The staple cartridge 220 defines a plurality of staple slots 225 and a slot 282 corresponding to the slots in the channel 218 and anvil 204.

The anvil assembly, cartridge assembly, or both, are pivotably movable. For example, the anvil 204 has protrusions 301 that are received in recesses 302 in the channel 218 so that the anvil 204 can pivot with respect to the cartridge assembly 230. In this way, tissue can be clamped between the anvil assembly 207 and the cartridge assembly 230.

Figure 5:
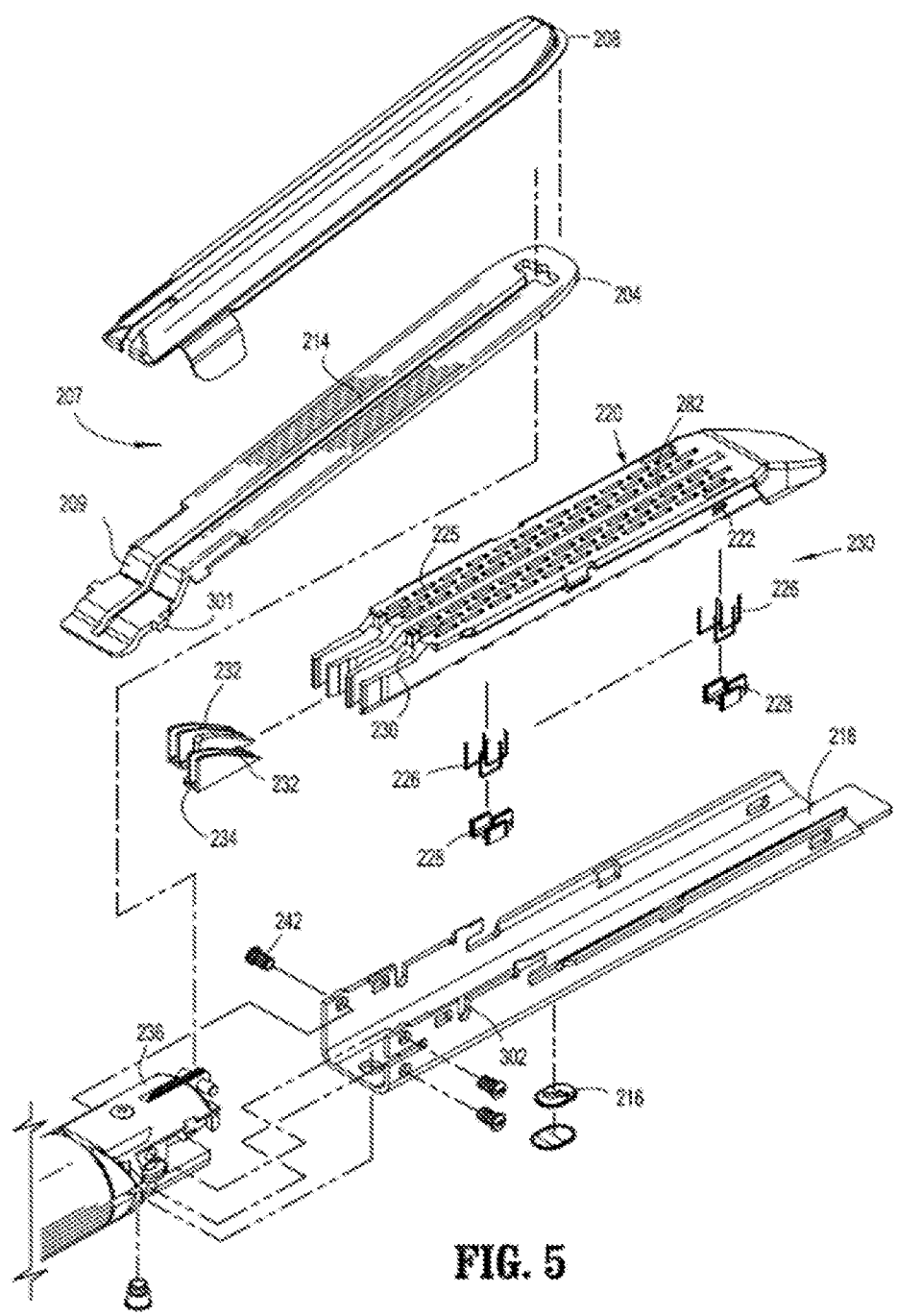
FIG. 5 is an exploded perspective view of part of a loading unit according to certain embodiments of the disclosure.
Figure 6:
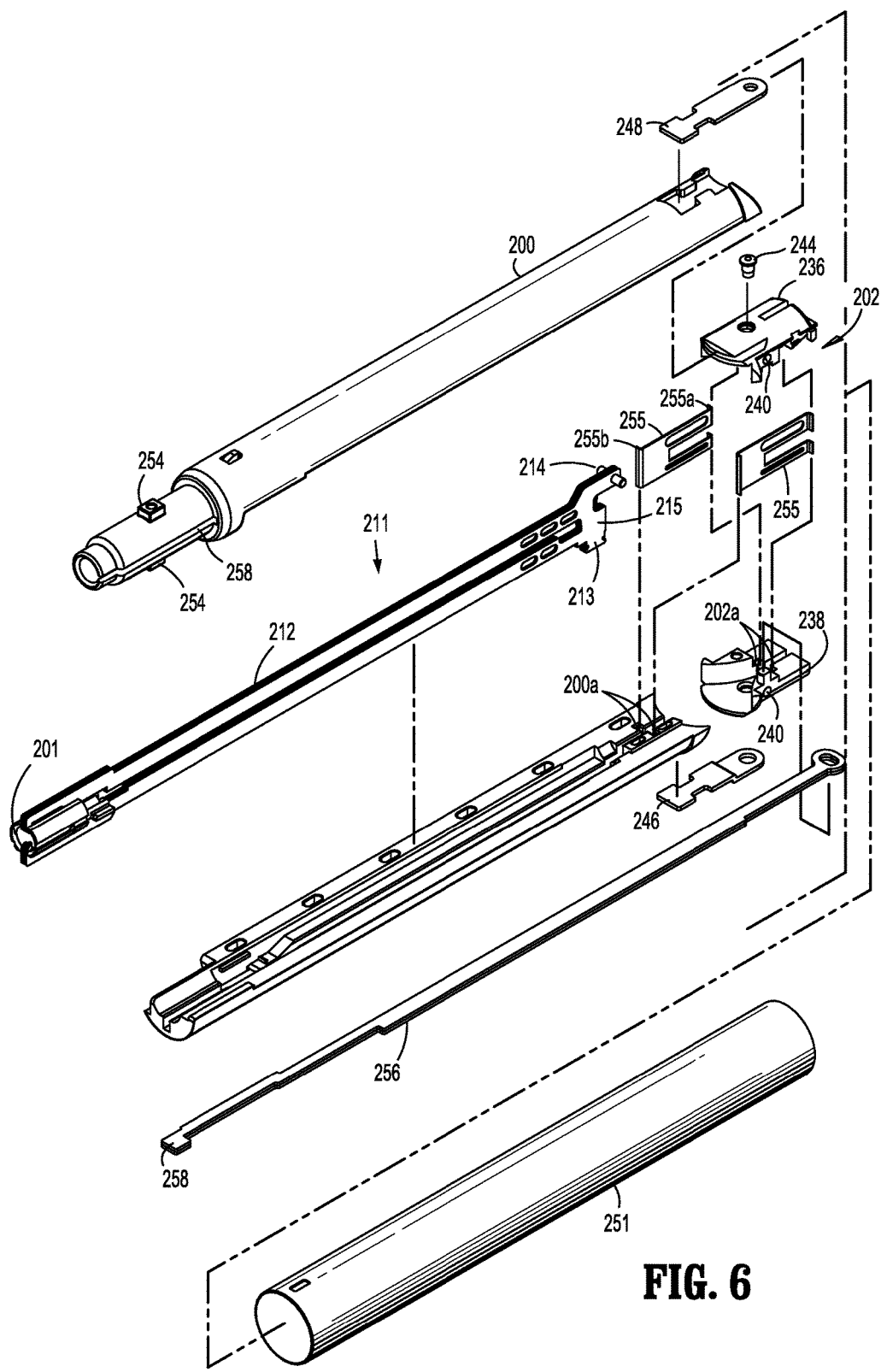
FIG. 6 is an exploded perspective view of part of a loading unit according to certain embodiments of the disclosure.
Figure 7:
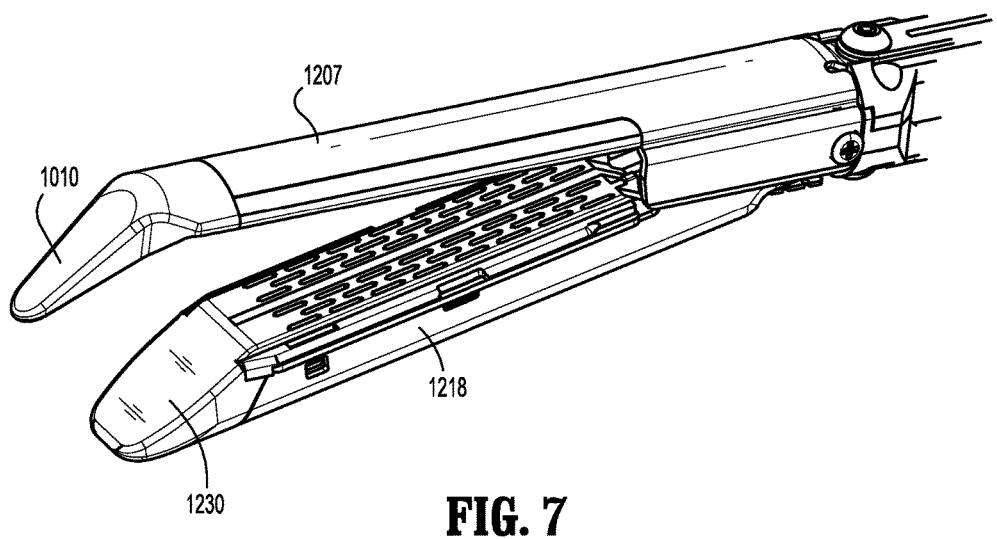
FIG. 7 is a perspective view of part of a loading unit according to certain embodiments of the disclosure.
Figure 8:
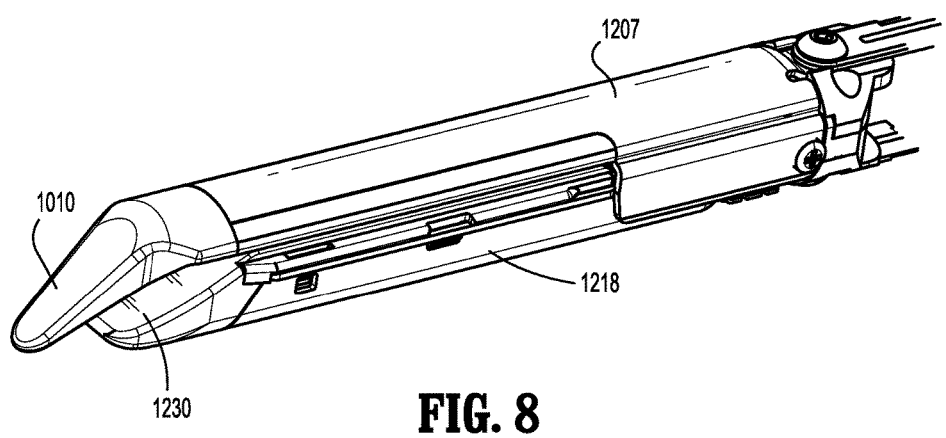
FIG. 8 is a perspective view of part of a loading unit according to certain embodiments of the disclosure.

Referring to FIGS. 5 and 6, a mounting assembly 202 is pivotally secured to the distal end of body 200, and is configured to be attached to the proximal ends of the jaws of the loading unit 20 such that pivotal movement of mounting assembly 202 about an axis perpendicular to the longitudinal axis of housing portion 200 effects articulation of the pair of jaws.

Referring to FIG. 6, mounting assembly 202 includes upper and lower mounting portions 236 and 238. Each mounting portion includes a threaded bore 240 on each side thereof dimensioned to receive threaded bolts 242 for securing the proximal end of channel 218 thereto. A pair of centrally located pivot members 244 extends between upper and lower mounting portions via a pair of coupling members 246 which engage the distal end of housing portion 200. Coupling members 246 each include an interlocking proximal portion 248 configured to be received in grooves 250 formed in the proximal end of housing portion 200 to retain mounting assembly 202 and body 200 in a longitudinally fixed position in relation thereto.

A pair of blow out plates 255 are positioned adjacent the distal end of body 200 adjacent the distal end of axial drive assembly to prevent outward bulging of drive assembly during articulation of the pair of jaws. Each blow-out plate 255 includes a planar surface which is substantially parallel to the pivot axis of the pair of jaws and is positioned on a side of drive assembly to prevent outward bulging of drive member 211. Each blow-out plate includes a first distal bend 255a which is positioned in a respective first groove 202a formed in mounting assembly 202 and a second proximal bend 255b which is positioned in a respective second groove 200a formed in a distal end of housing portion 200.

Staples 226 are disposed in the staple slots 225 and are driven out of those staple slots by pushers 228. The vertical portion 215 also extends through slot 214 to locate the upper flange or roller 214 on an upper surface of the anvil 204. A sled 234 is positioned in the staple cartridge initially in a proximal position, and has wedges 232 that engage the pushers 228. The pushers have camming surfaces (not shown) so that as the sled 234 is advanced by the drive beam 212 and clamping member 213, the sled will lift the pushers, driving the staples out of the slots 225, through tissue, and against staple forming recesses in the anvil 204. As the drive beam 212 and clamping member 213 is initially advanced, the upper flange or roller rides along the ramped surface 209 to approximate the anvil assembly 207 with the cartridge assembly 230. As the staples are fired, the drive beam 212 and clamping member 213 continue to engage the anvil assembly and cartridge assembly to maintain the position of the anvil assembly and cartridge assembly during firing of the staples.

In any of the embodiments disclosed herein, the clamping member may be an I-beam with integrally formed upper and lower flanges, the clamping member being attached to the drive beam at a distal end of the drive beam by welding or a similar method.

The loading unit 20 can include a first data connector for connection with a second data connector on the adapter assembly 100, to feed data back to a controller 9 in the handle portion 10. The first data connector can comprise contacts on the body 200 of the loading unit, whereas the second data connector can be contacts arranged on the adapter assembly 100 to connect with the contacts of the first data connector. A memory unit is disposed in the loading unit and is connected to the first data connector. The memory unit can comprise an EEPROM, EPROM, or the like, contained in the body 200 and can hold information such as the type of loading unit, the size of the staples in the loading unit, the length of the staple line formed by the loading unit when the staples are fired, and information about whether the loading unit has already been fired. The second data connector is connected to the controller 9 in the handle assembly by wires that extend through the adapter assembly, or via wireless connection. Alternatively, the memory unit of the loading unit can communicate wirelessly with the controller in the handle portion.

The controller can be an integrated circuit, analog or logic circuitry, and/or microprocessor. The controller receives information from the loading unit memory unit, other sensors in the adapter assembly and/or loading unit, and can control the operation of the surgical device. For example, sensors 222 can be provided in loading unit 20 to detect the clamping forces at the cartridge assembly and anvil assembly. The controller can initiate a visual or audible alarm in the event that recommended forces are exceeded, or the controller can cease operation of the surgical device by halting the motor of the handle assembly. A removable memory chip or card can also be included.

Where loading units 20 having different staple line lengths are available for use with the surgical device, identifying the length of the staple line and using that information to control the operation of the surgical device can be useful. For example, the controller 9 receives the staple line length from the memory unit and through the first data connector on the loading unit. That information is compared with data from the memory unit 11 in the handle portion 10 to determine how far to drive the staple drive shaft 148 and avoid driving that shaft 148 too far, and potentially damaging the loading unit. The type of loading unit, and the staple line length, staple size, etc., can therefore be used to control the operation of the surgical device. The controller 9 can be programmed to reverse the direction that the stapling drive cable 134 is driven after the staple line length is reached, thereby reversing the direction of the stapling drive shaft 148 and allowing the jaws of the loading unit to open. Alternatively or additionally, sensors can be provided in the loading unit to determine the position of the sled 234, clamping member 213, and/or drive beam 212, and to reverse the direction of the motor when the end of the staple line has been reached.

The handle portion 10 supplies power to the motor assembly 5 through a battery, generator, or electrical socket in order to drive the rotation of the cables 134, 136. The amount of torque required to clamp the jaws of the loading unit onto tissue can be detected by sensor 7 of handle portion 10, by monitoring the motor current. During clamping of tissue, during the initial movement of the clamping member 213 over the ramped surface 209 of the anvil 204, the clamping member 213 exerts forces on the anvil 204, and on the tissue being clamped between the cartridge assembly and anvil assembly. These forces can be detected by the controller 9, and characterized. For example, the force of the anvil in clamping tissue against the cartridge 220 can be detected and compared to data in the memory unit 11 of the controller, and used to provide information to the surgeon. Also, this information can be saved and reported for later use. The handle portion 10 desirably has a display unit and/or indicator for displaying information or alerting the user of the surgical device. Additionally or alternatively, the device can include an audio component for sounding an audible alarm or recorded message. The display can be a light emitting diode, liquid crystal display or any other display.

An encoder or encoders can be used as one of the sensors of the surgical device. The encoder includes Hall effect devices mounted adjacent the drive shafts from the motors, to detect a magnet or magnets mounted on the shafts. In this way, the angular position of the drive shafts and their direction, as well as the position of the drive shafts, drive cables 134, 136, articulation drive bar 154, and/or stapling drive shaft 148 can be determined. It is contemplated that, in any of the embodiments disclosed herein, there are encoders or other sensors provided for the drive cables 134, 136, articulation drive bar 154, and/or stapling drive shaft 148.

Sensors 222 can also be provided in the loading unit 20 to determine the gap between the staple cartridge 220 and anvil 204. The controller can include tables of information that indicate the desired gap for a particular loading unit and can be used to prevent the firing of staples in the event that the desired gap cannot be achieved. For example, U.S. Publication No. 2012/0211542, the disclosure of which is hereby incorporated by reference herein, discloses tissue management modes for controlling a surgical device and utilizes stored correlation tables. In any of the embodiments disclosed herein, the surgical device can include a controller and sensors in the adapter assembly 100, loading unit 20, and/or handle portion 10 that determine the clamping force, the gap between the cartridge 220 and anvil 204, whether the loading unit has been used, the type of loading unit, and/or the staple line length or size. The information is used to control the operation of the surgical device, provide some indication to the user, and/or is simply stored for later use.

In any of the embodiments disclosed herein, the loading unit has a mechanical feature for determining the type of cartridge 220, the staple line length, size of the staples, etc. The mechanical feature is a specially shaped bump, depression, or series of bumps or depressions, that are unique to that type of loading unit. The mechanical feature can have different shapes and/or textures, can determine staple size, staple line length, or both. It can also be used to determine other aspects of the loading unit, such as whether it is articulating or non-articulating. The mechanical feature can be a coating on the loading unit, that provides texture, a different frictional resistance, or some other aspect that can differentiate the type of loading unit.

Figure 9:
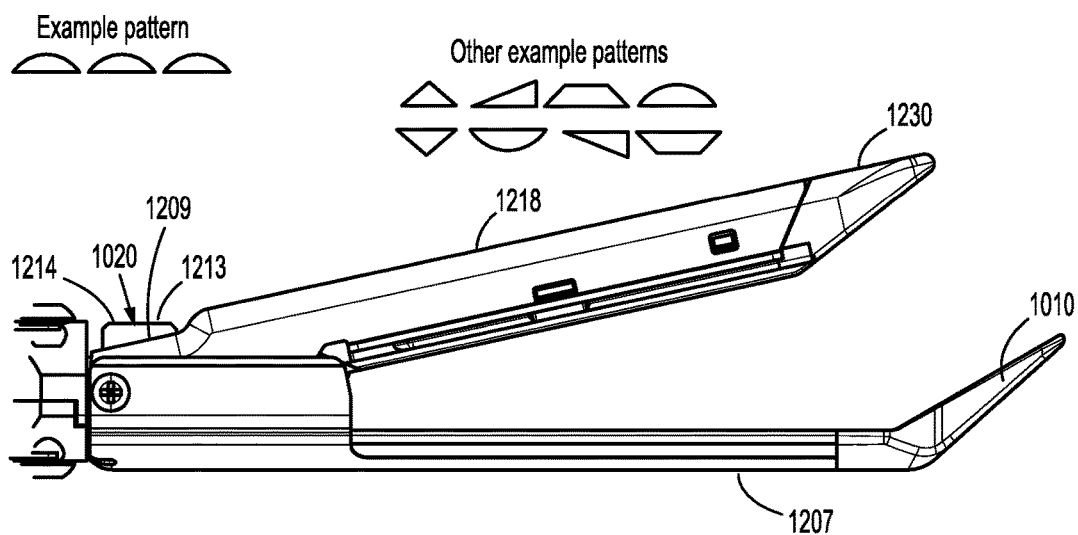
FIG. 9 is a side elevation view of a loading unit according to certain embodiments of the disclosure.

The mechanical feature 1020 is located on the loading unit at a location where the clamping member 213 engages the cartridge assembly 230, anvil assembly 204, or both. As shown in FIG. 9, a loading unit having an anvil assembly 1207 and cartridge assembly 1230, also has a dissecting tip 1010. In the initial advancement of the clamping member 1213, the clamping member upper flange or roller 1214 traverses the ramped surface 1209. The mechanical feature or features 1020 provided on the ramped surface 1209 change the force or torque at the motor. A blow up of examples of the mechanical features is shown in FIG. 9. The change in force or torque is detected by the controller of the handle portion and compared to data in the memory unit 11 of the controller. Using this information, the controller 9 determines that the loading unit has a 45 millimeter staple line length, for example, and drives the stapling drive cable 134 a predetermined number of rotations, to drive the stapling drive shaft 148 the distance necessary for driving all of the staples, but not exceeding the length of the cartridge assembly 1230. In addition, it can be determined that the loading unit is an articulating loading unit, allowing the articulation drive cable 136 to be driven. If it is determined that the loading unit is not an articulating loading unit, the articulation drive cable 136 is prevented from being driven by not turning on the corresponding motor in the motor assembly 5. For example, a mechanical feature or features 1020 can be provided on the channel 1218 that identify the type of loading unit, staple line length, staple size, or identify the loading unit as articulating. Similarly, a mechanical feature or features 1020 can be provided on the channel 1218 and/or anvil surface that identify the loading unit as having a buttress preloaded onto the loading unit, or identify the loading unit as one that has a dissecting tip.

In any of the embodiments disclosed herein, the mechanical feature 1020 can be provided on the anvil assembly 1207, cartridge assembly 1230, or both, in an area that is proximal to the ramped surface 1209. In this way, the user of the surgical device can determine the type of loading unit before clamping occurs. In any of the embodiments disclosed herein, electronic sensors, optical sensors, magnetic sensors, and/or any other kind of sensors, can be used in addition to the mechanical feature 1020 to provide information about the particular loading unit and its use. In any of the embodiments disclosed herein, an electronic sensor, magnetic sensor, optic sensor, or other sensor, is provided on the upper flange or roller 214, anvil 204, channel 218, or any combination thereof, to indicate the type of loading unit, staple size, staple line length, other aspects of the loading unit, and/or whether the loading unit has been fired or previously used.

Figure 10:
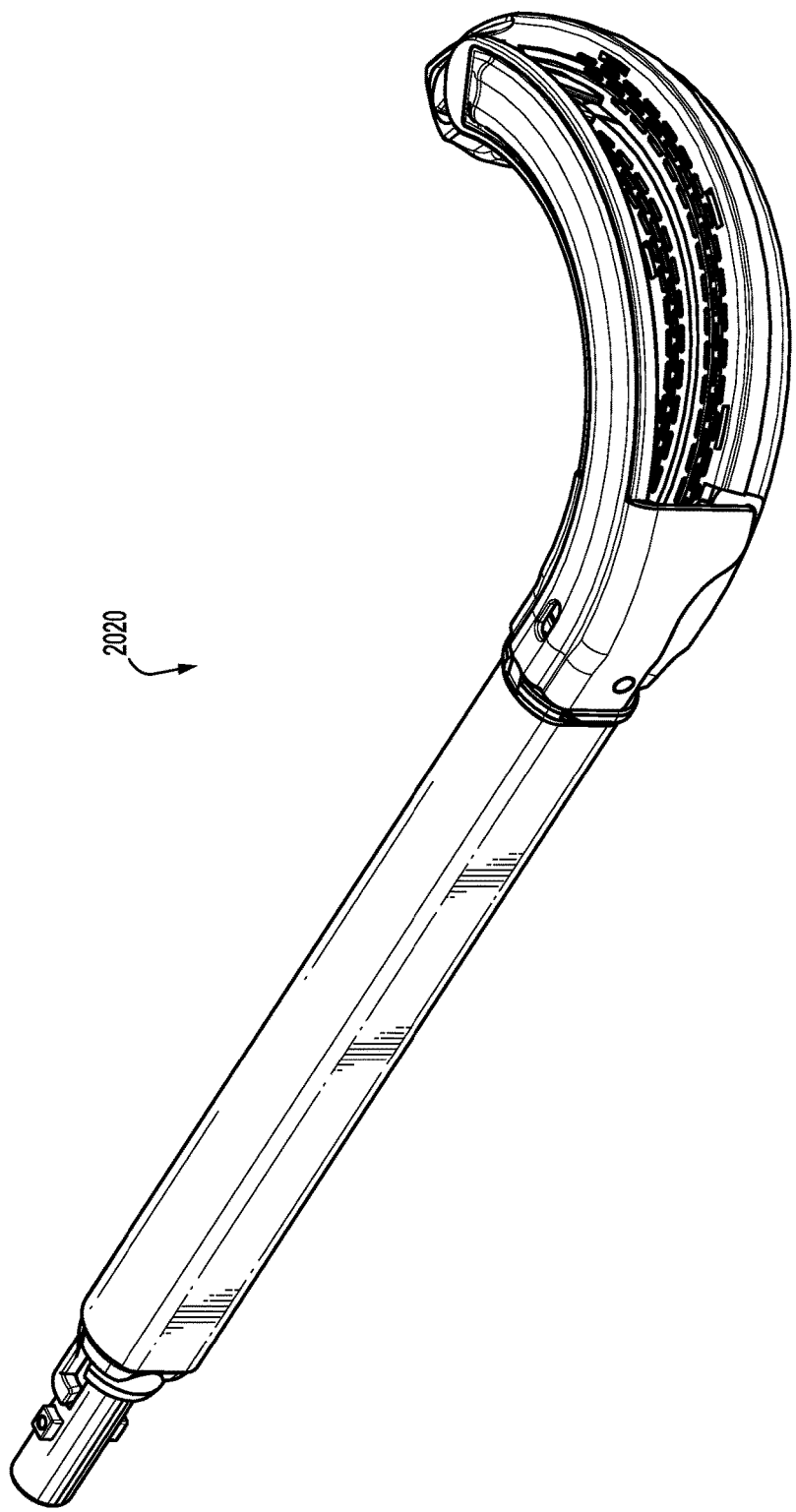
FIG. 10 is a perspective view of a loading unit according to certain embodiments of the disclosure.

FIG. 10 shows another loading unit 2020 having an anvil assembly and cartridge assembly that are curved. The curved loading unit 2020 has a clamping member and drive beam like that described above. Mechanical features are used to determine the type of loading unit, size of staples, length or diameter of the staple line, etc. as described above.

What is claimed is:

1. A surgical device, comprising:
   a handle portion;
   an elongate portion including an adapter assembly having a distal end and a proximal end, the proximal end configured to removably connect to the handle portion;
   a loading unit removably connected to the distal end of the adapter assembly of the elongate portion, the loading unit having a cartridge assembly, an anvil assembly, and a stapling drive member with a flange that engages at least one of the cartridge assembly or the anvil assembly, the loading unit having a body portion;

a motor assembly coupled to and configured to move the stapling drive member;

a ramped surface on the at least one of the cartridge assembly or the anvil assembly, the ramped surface being arranged to be traversed by the flange and to effectuate an approximation of the cartridge assembly and the anvil assembly;

a mechanical feature provided on the ramped surface and being configured for engagement by the flange as the flange traverses the ramped surface, the mechanical feature being indicative of an aspect of the loading unit; and a controller coupled to the motor assembly, the controller configured to determine the aspect of the loading unit based on a change in at least one property of the motor assembly due to contact between the flange and the mechanical feature upon advancement of the flange to engage the at least one of the cartridge assembly or the anvil assembly to approximate the anvil assembly with the cartridge assembly.

2. The surgical device according to claim 1, wherein the elongate portion has at least one drive member for connecting to and driving the stapling drive member.

3. The surgical device according to claim 1, wherein the controller is disposed in the handle portion.

4. The surgical device according to claim 3, wherein the controller includes a memory unit.

5. The surgical device according to claim 4, wherein the loading unit has a sensor for determining clamping pressure.

6. The surgical device according to claim 5, wherein the clamping pressure is saved in the memory unit.

7. The surgical device according to claim 1, wherein the loading unit has a sensor for determining the gap between the anvil assembly and cartridge assembly.

8. The surgical device according to claim 1, wherein the handle portion includes the motor assembly, the motor assembly having an output shaft.

9. The surgical device according to claim 8, wherein the handle portion includes a sensor for determining the torque on the output shaft of the motor assembly.

10. The surgical device according to claim 1, wherein the controller monitors a current of the motor assembly.

11. The surgical device according to claim 1, wherein the mechanical feature is selected from a group consisting of a coating, a texture, a depression, and a protrusion.

12. The surgical device according to claim 1, wherein the mechanical feature is selected from a group consisting of depressions, depressions and protrusions, and protrusions.

13. The surgical device according to claim 1, wherein the anvil assembly includes an anvil with a ramped surface.

14. The surgical device according to claim 13, wherein the mechanical feature is defined on the ramped surface.

15. The surgical device according to claim 13, wherein the mechanical feature is proximal to the ramped surface.

16. The surgical device according to claim 14, wherein the mechanical feature includes at least one of a specially shaped bump, a depression, a series of bumps, of a series of depressions.

17. The surgical device according to claim 14, wherein the mechanical feature includes a series of specially shaped bumps.

18. The surgical device according to claim 1, wherein the cartridge assembly has a channel.

19. The surgical device according to claim 18, wherein the mechanical feature is defined on the channel.

20. The surgical device according to claim 1, wherein the controller saves data concerning the use of the surgical device.

21. The surgical device according to claim 1, wherein the cartridge assembly has linear rows of staples.

22. The surgical device according to claim 21, wherein the mechanical feature indicates a length of the linear rows.

23. The surgical device according to claim 21, wherein the mechanical feature indicates a size of the staples.

* * * * *

UNITED STATES PATENT AND TRADEMARK OFFICE
CERTIFICATE OF CORRECTION

| | |
|---|---|
| PATENT NO. | : 10,478,182 B2 |
| APPLICATION NO. | : 13/961983 |
| DATED | : November 19, 2019 |
| INVENTOR(S) | : Taylor |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 870 days.

Signed and Sealed this
Twenty-fourth Day of November, 2020

Andrei Iancu
*Director of the United States Patent and Trademark Office*